United States Patent [19]

Brown et al.

[11] 4,331,653
[45] * May 25, 1982

[54] COMPOSITION FOR A TOPICAL CREAM FOR CURTAILING BLEEDING AND TREATING SKIN DISORDERS

[76] Inventors: Robert Brown, 3249 Greenfield Dr., Marietta, Ga. 30067; Jerome Setloff, 6851 Roswell Rd., Atlanta, Ga. 30328

[ * ] Notice: The portion of the term of this patent subsequent to Aug. 28, 1996, has been disclaimed.

[21] Appl. No.: 38,135

[22] Filed: May 11, 1979

Related U.S. Application Data

[63] Continuation-in-part of Ser. No. 825,853, Aug. 18, 1977, Pat. No. 4,166,108, which is a continuation-in-part of Ser. No. 764,405, Jan. 21, 1977, abandoned.

[51] Int. Cl.$^3$ .................. A61K 9/70; A61K 33/30; A61K 33/26; A61K 31/00
[52] U.S. Cl. .................. 424/28; 424/145; 424/147; 424/153; 424/154; 424/65; 424/66; 424/68; 424/DIG. 5; 424/170; 424/171; 424/172; 424/67; 424/289; 424/295; 424/315
[58] Field of Search .............. 424/28, 45, 145, 147, 424/153, 154, DIG. 5, 65, 66, 67, 170, 171, 172, 289, 295, 315

[56] References Cited

U.S. PATENT DOCUMENTS

3,343,540  9/1967  Siegel .................. 128/269
4,166,108  8/1979  Brown et al. .................. 424/28

OTHER PUBLICATIONS

"Atlas Surfactant and Sorbital", pp. 7, 9 and 44 of formulary of typical pharm. formulations for topical application.

*Primary Examiner*—Donald B. Moyer
*Attorney, Agent, or Firm*—L. Lawton Rogers, III

[57] ABSTRACT

An improved styptic composition which effectively curtails bleeding while administering a soothing sensation on the injured area. The styptic composition is in the form of a stable lotion or cream having the following general formula:
(1) from about 2% to about 12% by weight of a long chain fatty acid;
(2) from about 0.4% to about 3.5% by weight of a wax filler;
(3) from about 1% to about 10% by weight of polyethylene glycol stearate;
(4) from about 1% to about 5% by weight of polyethylene glycol sorbitan beeswax; and,
(5) from about 0.5% to about 25% by weight of an acidic metallic salt,
(6) the balance being water.

Optionally, from about 1% to about 4% by weight of glycerin may be added as a humectant.

Any conventional antiseptic may also be added to the composition.

The styptic composition may be packaged in any convenient form including jars, bottles, tubes, pump applicators, aerosol canisters and can also be impregnated into pre-packaged bandages.

The composition has been found useful in the treatment of certain skin disorders such as I and D of cystic acne lesions, chicken pox, seborrhea, bleeding contact dermatitis, hemorrhoids, chapped lips, and the like.

28 Claims, No Drawings

COMPOSITION FOR A TOPICAL CREAM FOR CURTAILING BLEEDING AND TREATING SKIN DISORDERS

CROSS-REFERENCE TO RELATED APPLICATIONS

This application is a continuation-in-part of co-pending application Ser. No. 825,853, filed Aug. 18, 1977, now U.S. Pat. No. 4,166,108, dated Aug. 28, 1979, which was in turn a continuation-in-part of then pending application Ser. No. 764,405, filed Jan. 21, 1977, and now abandoned.

BACKGROUND OF THE INVENTION

This invention relates to a novel styptic composition which quickly and effectively stanches the flow of blood from a wound without causing irritation to the skin.

The use of styptic or astringent compositions is well established in the art. As originally formulated, the compositions were comprised of highly acidic salts of such metals as iron, zinc or aluminum that were employed as a powder or shaped in the form of a stick or pencil. Typical styptic compositions in stick form are set forth in the U.S. Pat. Nos. 459,738, 497,659 and 819,901.

In use, the acidic salts effectively curtailed the bleeding in the injured area by causing the adjacent blood vessels to constrict. Unfortunately, the acidic nature of the salts also caused a stinging sensation which often exceeded the pain caused by the original wound. The use of these styptic compositions was therefore restricted to very minor wounds, such as those received in shaving. If the composition was applied to a major wound, the pain accompanying the application would often send the injured person into shock. Of course, less acidic compositions, which caused less pain, could be utilized. However, such compositions had a markedly reduced effectiveness in curtailing bleeding.

A second drawback of some of the highly acidic compositions is its deleterious effect on any clothing with which it may come into contact. According to the type of composition and fabric, the clothing could be indelibly stained or even deteriorated.

In an attempt to obviate these problems, liquid styptic compositions were formulated. It was hoped that by combining an acidic salt with a volatile solvent, the evaporation of the solvent would offset the stinging nature of the salt. See, for example, U.S. Pat. Nos. 2,118,225 and 3,343,540. While the evaporation of the solvent took some of the pain out of the application of the styptic compound, it was found that the amount of styptic necessary to stop the flow of blood still caused a great deal of discomfort and hence precluded its use in major wounds.

Aerosols, emitting a liquid or a powder, were also attempted, as shown in U.S. Pat. Nos. 3,624,201, 3,863,005, 3,928,556 and British Patent No. 1,254,534. Although the aerosol containers greatly simplified the application of the styptic composition and kept the composition sterile, the stinging problem associated with effective bleeding curtailment persisted.

It is also known in the art to prepare creams or lotions containing acidic metallic salts which are stable and hence do not separate into an oil phase and an aqueous phase. These creams or lotions, however, do not relate to styptic compositions. For example, U.S. Pat. No. 2,492,085 discloses an astringent composition which is in the form of a stable cream or lotion. The stated advantages of this composition are its non-irritating action upon the skin and non-deteriorating effect upon clothing. These advantages are explained as resulting from the use of aluminum chlorohydrate which has a low acidity in comparison with stronger aluminum salts, such as aluminum sulfate. The non-irritating action of the composition is restricted to its intended use as a deodorant. While it is almost inconceivable that a deodorant composition would be used as a styptic composition, if such a composition were applied to an open wound, a great amount of pain would result.

Another antiperspirant composition is disclosed in U.S. Pat. No. 3,235,458, which is directed to an emulsified cosmetic cream. Like other deodorants or antiperspirants, a great amount of pain would result from the application to an open wound, and most commercial astringents or antiperspirants are sold with an express caveat against application to broken skin.

Creams or lotions containing the highly acidic salt aluminum sulfate are often unstable. As shown by the large number of compositions listed by commercial companies, it is well known that such compounds are not equivalent or readily substituted one for another. See, for example, pages 7, 9 and 44 of *Atlas Surfactants and Sorbitol*, published by the Atlas Powder Company and available in the Scientific Library of the U.S. Patent and Trademark Office.

It is further known to prepare cosmetic gels which contain a variety of metallic salts in combination with a high molecular weight of polyvinyl alcohol and methyl cellulose. See, for example, U.S. Pat. No. 3,856,941. While highly acid salts are employed, the patent does not disclose the formation of a cream or lotion, nor does it suggest that the gel can be applied to injured areas to curtail bleeding without irritation.

It is important to note that the terms "astringent" and "styptic" are not synonymous, and further that a "non-sting styptic composition" is clearly different from a "styptic composition". As stated on pages 716–719, and 768 of *Remington's Pharmalogical Sciences*, 15th Edition, 1975, published by Mack Publishing Company of Easton, Penn., many astringents are irritants or caustic in moderate to high concentrations. This is particularly important where the application of the composition is to broken skin.

It therefore an object of the present invention to provide a novel styptic composition which overcomes or substantially alleviates the problems of the prior art.

It is another object of the present invention to provide a novel styptic composition which does not sting when applied to a wound.

It is another object of the present invention to provide a novel styptic composition which does not stain the clothing.

It is yet another object of the present invention to provide a novel styptic composition in the form of a cream or lotion which is highly stable.

It is a further object of the present invention to provide a novel styptic composition having the following general formula:

(1) from about 2% to about 12% by weight of a long chain fatty acid;
(2) from about 0.4% to about 3.5% by weight of a wax filler;

(3) from about 1% to about 10% by weight of polyethylene glycol stearate;
(4) from about 1% to about 5% by weight of polyethylene glycol sorbitan beeswax; and,
(5) from about 0.5% to about 25% by weight of an acidic metallic salt,
(6) the balance being water.

It is a further object of the present invention to provide a novel styptic composition according to the above general formula which contains the optional ingredients glycerin and an antiseptic.

It is a further object of the present invention to provide a pressurized aerosol container to distribute a novel styptic composition.

It is still a further object of the present invention to provide a pre-packaged bandage which is impregnated with a novel styptic composition.

These and other objects, as well as the scope, nature and utilization of the invention, will be apparent to those skilled in the art from the following description and appended claims.

DESCRIPTION OF THE PREFERRED EMBODIMENT

The novel, non-sting styptic composition of the present invention is in the form of a stable lotion or cream. The components other than the acidic metallic salt and the consistency of the lotion or cream exert a soothing and cooling sensation on the injured area which effectively overcomes the stinging sensation caused by the highly acidic metallic salt. The ability of the salt to curtail the bleeding of the wound, however, is not affected by the balance of the components in the lotion or cream. Thus, the styptic composition not only stops the flow of blood, but it does so with an attendant soothing sensation. Of course, if applied to major wounds, a slight stinging sensation will occur. The degree of pain, however, is far below that caused by known styptic compositions and can readily be tolerated without the fear of shock occurring.

A further surprising feature of the present invention is the stability of the lotion or cream. In most instances, when an acidic composition is added to an emulsion of an oleaginous material and an aqueous mixture, the emulsion rapidly breaks down into the two phases. In contradistinction to this normal occurrence, the styptic composition of the present invention exists as stable emulsion which can be stored on a shelf for months without phase separation occurring.

The stable lotion or cream has the following general formula:
(1) from about 2% to about 12% by weight of a long chain fatty acid;
(2) from about 0.4% to about 3.5% by weight of a wax filler;
(3) from about 1% to about 10% by weight of polyethylene glycol stearate;
(4) from about 1% to about 5% by weight of polyethylene glycol sorbitan beeswax; and,
(5) from about 0.5% to about 25% by weight of an acidic metallic salt,
(6) the balance being water.

A preferred styptic composition has the following general formula:
(1) from about 4% to about 11% by weight of a long chain fatty acid;
(2) from about 1% to about 3% by weight of a wax filler;
(3) from about 4% to about 7% by weight of polyethylene glycol stearate;
(4) from about 2% to about 4% by weight of polyethylene glycol sorbitan beeswax; and
(5) from about 5% to about 20% by weight of an acidic metallic salt,
(6) the balance being water.

The above formulas are unique in that they combine the attributes of an effective styptic composition with the desired non-sting, non-stain characteristics not found in the prior art. These advantages are believed to flow from the form of the styptic composition, namely a stable lotion or cream.

The long chain fatty acid, polyethylene glycol stearate and polyethylene glycol sorbitan beeswax are employed as emulsifiers or dispersing agents which promote the formation of the stable lotion or cream. Polyethylene glycol stearate, for example, is a non-ionic emulsifier and dispersing agent which consists of a water soluble polyoxyethylene derivative of stearic acid. This compound can be purchased under the trade name Myrj-52 manufactured by Atlas Powder Company. Polyethylene glycol sorbitan beeswax is an analogous compound, i.e, a polyoxyethylene (20) sorbitol beeswax derivative, which can be purchased under the trade name Atlas G-1726 which is also manufactured by Atlas Powder Company. While the exact mechanism is not completely understood, the polyethylene glycol stearate and polyethylene glycol sorbitan beeswax are also believed to be primarily responsible for the soothing nature of the lotion or cream.

The term "long chain fatty acid" as used herein includes those unsaturated or saturated fatty acids having from nine to twenty-three carbon atoms in the molecule. The saturated fatty acids are preferred for purposes of the present invention. The unsaturated fatty acids, e.g. oleic acid, exhibit a tendency to oxidize and thus are typically employed in conjunction with a conventional anti-oxidant. Exemplary of such anti-oxidants are butylated hydroxyanisole, butylated hydroxytoluene and propyl gallate. While the specific amount of anti-oxidant which is added to the composition containing an unsaturated fatty acid will depend on the particular anti-oxidant utilized, about 0.02% based on the weight of the long chain unsaturated fatty acid has generally been found to yield acceptable results. Exemplary of saturated fatty acids are lauric, palmitic and, preferably, stearic acid. As may be seen from the above general formula, the amount of fatty acid incorporated into the composition may vary from about 2% to about 12% of the total weight of the composition. When a fatty acid having a longer carbon chain is employed, a lesser amount is required which approaches the lower limit of the range as the length of the carbon chain approaches twenty-three carbon atoms. Conversely, if a fatty acid having a shorter carbon chain is employed, a greater amount is required. The precise amount of a specific fatty acid in the composition can readily be determined by routine experimentation by those of ordinary skill in the art.

The term "wax filler" defines various wax products which increase the viscosity or consistency of the lotion or cream. Typical of such wax products are microcrystalline wax, paraffin wax and, preferably, beeswax.

The term "acidic metallic salt" as used herein includes those metal salts which exhibit a degree of acidity sufficient to stanch the flow of blood yet may be formulated into a stable lotion or cream. Typical of such acidic salts are the chloride, sulfate, phenolsulfonate and chlorohydrate salts of aluminum, zinc and iron, either as a simple salt or as a dibasic salt as in the case of aluminum potassium sulfate. The preferred salts are those having aluminum contained therein, particularly aluminum ammonium sulfate, aluminum potassium sulfate and, as the most preferred acidic metallic salt, aluminum sulfate. Combinations of salts may also be employed. It will be apparent to those of ordinary skill in the art upon a perusal of the list of possible acidic metallic salts that they do not all exhibit the same degree of acidity. Accordingly, a greater amount of a less acidic metallic salt will be required in the composition than in the case of a more acidic metallic salt. The precise amount of acidic metallic salt must be selected such that the composition is effective in curtailing bleeding without causing an inordinate amount of pain when applied. These criteria create a variation in the time needed to completely stop the bleeding, the most preferred acidic metallic salt, namely aluminum sulfate, being the most effective in curtailing bleeding without causing pain. In all instances, however, the amount of acidic metallic salt required in the composition will fall within the limits established by the above formula.

The following Examples are given as specific illustrations of the invention. It should be understood, however, that the invention is not limited to the specific details set forth therein. In the following Examples, all percentages are by weight of the total composition.

EXAMPLE I

| (1) | Stearic Acid | 7.5% |
|---|---|---|
| (2) | Beeswax | 1.7% |
| (3) | Polyethylene glycol stearate | 5.3% |
| (4) | Polyethylene glycol sorbitan beeswax | 3.5% |
| (5) | Aluminum sulfate | 13% |
| (6) | Water | 69% |

EXAMPLE II

| (1) | Palmitic acid | 9% |
|---|---|---|
| (2) | Microcrystalline Wax | 2.5% |
| (3) | Polyethylene glycol stearate | 3.8% |
| (4) | Polyethylene glycol sorbitan beeswax | 2.3% |
| (5) | Aluminum Potassium Sulfate | 10% |
| (6) | Water | 72.4% |

EXAMPLE III

| (1) | Lauric acid | 11% |
|---|---|---|
| (2) | Paraffin Wax | 3.0% |
| (3) | Polyethylene glycol stearate | 6.2% |
| (4) | Polyethylene glycol sorbitan beeswax | 4% |
| (5) | Zinc Sulfate | 18% |
| (6) | Water | 57.8% |

A humectant may optionally be present in an amount ranging from about 1% to about 4% by weight. Although the humectant does not affect the ability of the styptic lotion or cream to stanch the flow of blood, it is generally incorporated into the composition to prevent the lotion or cream from drying out. Typical of the humectants which may be employed are the polyhydric aliphatic compounds. Glycerin is the preferred humectant.

Any conventional antiseptic may also be incorporated into the composition. Such antiseptics include the quaternary ammonium compounds and the alcohol compounds including phenol compounds. One preferred antiseptic composition is hexylresorcinol. The amount of antiseptic utilized in the composition will depend on the particular compound employed. Since most known antiseptic compounds cause some degree of stinging, the amount of antiseptic utilized should be maintained at the minimum amount necessary to effectively prevent the growth of microorganisms. In the case of hexylresorcinol this amount is in the order of about 2% by weight.

The above mentioned ingredients may be combined in the following manner: long chain fatty acid, the wax filler, polyethylene glycol stearate, polyethylene glycol sorbitan beeswax and, optionally, glycerin are mixed together and heated to a temperature of about 70° C. After the mixture has reached this temperature, a warm (70° C.) aqueous solution of the highly acidic metallic salt is blended in. The mixture is then cooled while being agitated.

The resulting stable cream or lotion is an effective styptic composition which has a wide range of applications. In use, the cream or lotion is spread on the wound and is quickly absorbed by the skin. Therefore, if suturing is required or desired, it may be performed without having to clean the wound of the styptic composition. Due to its non-sting characteristic, the styptic composition of the present invention may be spread on minor cuts, abrasions and even major wounds without causing pain to the injured entity. The term "entity" is utilized to reflect the fact that the syptic composition of the present invention is effective on animals as well as humans. The composition can also be employed in the dental field if a flavoring agent is added and can be incorporated into first-aid kits for civilian and military use.

A second advantageous feature of the styptic composition of this invention is that it does not stain or deteriorate fabrics with which it comes in contact. This feature enables the composition to be applied to a small cut or abrasion on an area of skin which is normally covered by clothing without the need for a restrictive bandage or covering.

The cream or lotion which comprises the styptic composition of this invention can be packaged in any convenient container including jars, bottles, tubes, pump applicators and preferably, in pressurized aerosol canisters. The aerosol canisters which may be employed to distribute the lotion or cream are well known in the art so that a further exposition of the details of the canisters need not be set forth here (see for example, U.S. Pat. Nos. 2,631,814, 2,645,387 and 2,662,668, the contents of which are incorporated by reference). In an aerosol canister, the composition may be maintained in a sterile condition irrespective of the surrounding environment and may be directly applied where needed with a minimum of effort.

The styptic composition of the present invention may also be utilized to impregnate prepackaged bandages. The wound covering area of the bandages may be fabricated out of natural fibers, such as cotton, man-made fibers, such as polyester or rayon or mixtures thereof. According to the type of fabric employed, the bandage density and thickness and the type of wound intended to be covered, it is necessary to vary the amounts of the several components which comprise the styptic composition. However, such variation will fall within the ranges established above. In this form, the combination of the styptic composition and the bandage may be maintained in a sterile package. When required, it may be quickly opened and applied to the wound thereby stanching the flow of blood, easing the pain of the wound and initiating the healing process without delay. Such advantages make the impregnated bandage particularly suitable for first aid kits, emergency units, physician's bags and a variety of other locations.

The composition has been found to have great utility in the treatment of certain skin disorders, such as I and D of cystic acne lesions, chicken pox, seborrhea. Other uses include application to mucosal surfaces, to chapped lips, to combat nasal dryness and to heal bleeding contact dermatitis. A further application is in the treatment of hemorrhoids. In all such instances in which clinical experiments were conducted, the composition exhibited marked healing properties in a remarkably short time.

Although the invention has been described with reference to preferred embodiments, it is to be understood that variations and modifications may be employed without departing from the scope of the invention as defined in the following claims.

What is claimed is:

1. A non-sting styptic composition as a stable cream or lotion comprising:
   (1) from about 2% to about 12% by weight of a long chain fatty acid selected from the group saturated or unsaturated having from nine to twenty-three carbon atoms therein;
   (2) from about 0.4% to about 3.5% by weight of a wax filler;
   (3) from about 1% to about 10% by weight of polyethylene glycol stearate;
   (4) from about 1% to about 5% by weight of polyethylene glycol (20) sorbitan beeswax; and,
   (5) from about 0.5% to about 25% by weight of an acidic metallic salt, said acidic metallic salt being characterized by possessing a degree of acidity sufficient to stanch the flow of blood and being capable of being formulated into said stable cream or lotion,
   (6) the balance being water.

2. The styptic composition of claim 1, wherein the acidic metallic salt is selected from the group consisting of aluminum sulfate, aluminum potassium sulfate and aluminum ammonium sulfate.

3. The styptic composition of claim 2, wherein the acidic metallic salt is aluminum sulfate.

4. The styptic composition of claim 3, wherein the wax filler is beeswax.

5. The styptic composition of claim 4, wherein the long chain fatty acid is stearic acid.

6. The styptic composition of claim 1, wherein the wax filler is selected from the group consisting of beeswax, microcrystalline wax and paraffin wax.

7. The styptic composition of claim 1, wherein a humectant is present in an amount ranging from about 1% to about 4% by weight.

8. The styptic composition of claim 7, wherein the humectant is glycerin.

9. The styptic composition of claim 7 including an antiseptic.

10. A non-sting styptic composition as a stable cream or lotion as set out in claim 1 wherein the wax filler is selected from the group consisting of microcrystalline wax, paraffin wax and beeswax; and wherein the acidic metal salt is selected from the group consisting of aluminum phenolsulfonate, zinc phenolsulfonate, and ferric phenolsulfonate.

11. The composition of claim 1 wherein the acidic metal salt is selected from the group consisting of aluminum phenolsulfonate, zinc phenolsulfonate, and ferric phenolsulfonate.

12. The composition of claim 11, wherein the wax filler is beeswax.

13. The composition of claim 11, wherein a humectant is present in an amount ranging from about 1% to about 4% by weight.

14. The composition of claim 13, wherein the humectant is glycerin.

15. An improved styptic composition which does not sting or stain clothes when applied, and composition being in the form of a stable cream or lotion which includes:
   (1) from about 2% to about 12% by weight of a long chain fatty acid;
   (2) from about 0.4% to about 3.5% by weight of a wax filler;
   (3) from about 1% to about 10% by weight of polyethylene glycol stearate;
   (4) from about 1% to about 5% by weight of polyethylene glycol sorbitan beeswax; and,
   (5) from about 0.5% to about 25% by weight of an acidic metallic salt,
   (6) the balance being water.

16. A pressurized aerosol canister containing an improved non-sting, non-stain styptic composition, said styptic composition being in the form of a stable lotion or cream which includes:
   (1) from about 2% to about 12% by weight of a long chain fatty acid;
   (2) from about 0.4% to about 3.5% by weight of a wax filler;
   (3) from about 1% to about 10% by weight of polyethylene glycol stearate;
   (4) from about 1% to about 5% by weight of polyethylene glycol sorbitan beeswax; and,
   (5) from about 0.5% to about 25% by weight of an acidic metallic salt,
   (6) the balance being water.

17. The pressurized aerosol canister of claim 16, wherein the acidic metallic salt is selected from the group consisting of aluminum sulfate, aluminum potassium sulfate and aluminum ammonium sulfate.

18. The pressurized aerosol canister of claim 17, wherein the acidic metallic salt is aluminum sulfate.

19. The pressurized aerosol canister of claim 18, wherein the wax filler is beeswax.

20. The pressurized aerosol canister of claim 16, wherein the wax filler is selected from the group consisting of beeswax, microcrystalline wax and paraffin wax.

21. The pressurized aerosol canister of claim 16, wherein glycerin is present in an amount ranging from about 1% to about 4% by weight.

22. A bandage having a wound covering area composed of fibers selected from the group consisting of natural fibers, man-made fibers and mixtures thereof, said bandage including a non-sting, non-stain styptic composition, said styptic composition being in the form of a stable cream or lotion which includes:
   (1) from about 2% to about 12% by weight of a long chain fatty acid;

(2) from about 0.4% to about 3.5% by weight of a wax filler;
(3) from about 1% to about 10% by weight of polyethylene glycol stearate;
(4) from about 1% to about 5% by weight of polyethylene glycol sorbitan beeswax; and,
(5) from about 0.5% to about 25% by weight of an acidic metallic salt,
(6) the balance being water.

23. The bandage of claim 22, wherein the acidic metallic salt is selected from the group consisting of aluminum sulfate, aluminum potassium sulfate and aluminum ammonium sulfate.

24. The bandage of claim 23, wherein the acidic metallic salt is aluminum sulfate.

25. The bandage of claim 23, wherein the wax filler is beeswax.

26. The bandage of claim 22, wherein the wax filler is selected from the group consisting of beeswax, microcrystalline wax and paraffin wax.

27. The bandage of claim 22, wherein a humectant is present in an amount ranging from about 1% to about 4% by weight.

28. A non-sting styptic composition as a stable cream or lotion comprising:
(1) from about 2% to about 12% weight of a saturated or unsaturated long chain fatty acid having from nine to twenty-three carbon atoms therein and selected from the group consisting of oleic acid, lauric adic, palmitic acid and stearic acid;
(2) from about 0.4% to about 3.5% by weight of a wax filler selected from the group consisting of microcrystalline wax, paraffin wax and beeswax;
(3) from about 1% to about 10% by weight of polyethylene glycol stearate;
(4) from about 1% to about 5% by weight of polyethylene glycol (20) sorbitan beeswax; and,
(5) from about 0.5% to about 25% by weight of an acidic metallic salt selected from the group consisting of aluminum phenolsulfonate, zinc phenolsulfonate, and ferric phenolsulfonate, said acidic metallic salt being characterized by possessing a degree of acidity sufficient to stanch the flow of blood and being capable of being formulated into said stable cream or lotion,
(6) the balance being water.

* * * * *